US012544258B2

(12) United States Patent

Whitsett

(10) Patent No.: US 12,544,258 B2
(45) Date of Patent: Feb. 10, 2026

(54) AQUEOUS MICRO SHUNT

(71) Applicant: Jeffrey Whitsett, Houston, TX (US)

(72) Inventor: Jeffrey Whitsett, Houston, TX (US)

( * ) Notice: Subject to any disclaimer, the term of this patent is extended or adjusted under 35 U.S.C. 154(b) by 322 days.

(21) Appl. No.: 18/102,767

(22) Filed: Jan. 30, 2023

(65) Prior Publication Data

US 2024/0252350 A1 Aug. 1, 2024

(51) Int. Cl.
*A61F 9/00* (2006.01)

(52) U.S. Cl.
CPC .................................. *A61F 9/0017* (2013.01)

(58) Field of Classification Search
CPC ........................... A61F 9/0017; A61F 9/00781
See application file for complete search history.

(56) References Cited

U.S. PATENT DOCUMENTS 4,402,681 A * 9/1983 Haas .................. A61F 9/00781 604/9
5,127,901 A * 7/1992 Odrich ................ A61F 9/00781 604/9
5,868,697 A 2/1999 Richter et al.
6,450,984 B1 9/2002 Lynch et al.
6,626,858 B2 9/2003 Lynch et al.
7,613,543 B2 11/2009 Petersson et al.
8,920,357 B2 12/2014 Baerveldt
9,101,444 B2 8/2015 Pinchuk
9,301,875 B2 4/2016 Tu et al.
9,610,271 B2 4/2017 Cadden et al.
9,655,779 B2 5/2017 Bigler et al.
9,730,638 B2 8/2017 Haffner et al.
10,406,029 B2 9/2019 Tu et al.
10,736,778 B2 8/2020 Brown
10,980,667 B2 4/2021 Peyman
11,045,352 B2 6/2021 Peyman
2002/0177856 A1* 11/2002 Richter ............... A61F 9/00781 606/108

(Continued)

FOREIGN PATENT DOCUMENTS

CA 2530234 8/2004
CA 2872338 11/2013

(Continued)

*Primary Examiner* — Adam Marcetich
(74) *Attorney, Agent, or Firm* — Law Offices of Steven W. Weinrieb

(57) ABSTRACT

An aqueous micro shunt for treating dry eye syndrome comprises an axially oriented shaft, for insertion through a scleral wall portion of an eye and into an anterior chamber of the eye, and having an open distal end adapted to be fluidically connected to aqueous humor contained within the anterior chamber of the eye. First and second axially oriented lumens are defined within the axially oriented shaft, and a plate is fixedly mounted at a predetermined angle upon a proximal end of the axially oriented shaft. A slot is defined within the plate so as to be fluidically connected to the second axially oriented lumen defined within said axially oriented shaft such that aqueous fluid can flow from the anterior chamber of the eye, through the first and second lumens defined within the axially elongated shaft, and outwardly through the slot defined within the plate so as to flow over an ocular surface portion of the eye and thereby treat dry eye syndrome.

10 Claims, 4 Drawing Sheets

(56) References Cited

U.S. PATENT DOCUMENTS

2002/0188308 A1* 12/2002 Tu .......................... A61M 27/00 606/107
2003/0060752 A1* 3/2003 Bergheim ........... A61F 9/00781 604/27
2003/0229303 A1* 12/2003 Haffner ............... A61F 9/00781 604/8
2006/0189915 A1* 8/2006 Camras ............... A61F 9/00781 604/8
2007/0021762 A1 1/2007 Liu et al.
2007/0106200 A1 5/2007 Levy
2007/0156079 A1* 7/2007 Brown ..................... A61B 3/16 604/9
2009/0043321 A1 2/2009 Conston et al.
2010/0057055 A1* 3/2010 Camras ............... A61F 9/00781 604/540
2011/0105986 A1* 5/2011 Bronstein ........... A61F 9/00781 604/8
2013/0267887 A1 10/2013 Kahook et al.
2014/0236067 A1* 8/2014 Horvath .............. A61F 9/00781 604/9
2016/0302965 A1 10/2016 Erickson et al.
2017/0071791 A1 3/2017 Piven
2017/0348149 A1* 12/2017 Stergiopulos ....... A61M 27/002
2018/0161205 A1 6/2018 Tu et al.
2020/0179171 A1 6/2020 Crimaldi et al.
2020/0229979 A1 7/2020 Otaka
2020/0330272 A1 10/2020 Brown
2021/0220172 A1 7/2021 Brown
2021/0298948 A1 9/2021 Haffner et al.
2025/0099296 A1* 3/2025 Han ........................ A61L 27/14

FOREIGN PATENT DOCUMENTS

CN 103371885 10/2013
CN 104042401 A * 9/2014
EP 1184010 A2 * 3/2002 ......... A61F 9/00781

* cited by examiner

AQUEOUS MICRO SHUNT

FIELD OF THE INVENTION

The present invention relates generally to medical devices, and more particularly to a micro shunt which is adapted to be inserted into the subconjunctival space of the human eye so as to transit through the sclera of the human eye, and wherein a distal end portion of the shunt is adapted to be disposed within the anterior chamber of the eye, while a proximal end portion of the shunt is disposed externally of the eye, so as to permit aqueous humor to flow from the anterior chamber of the eye, outwardly through the micro shunt, transiting the conjunctiva, and to then flow over the corneal surface of the eye so as to effectively treat dry eye syndrome.

BACKGROUND OF THE INVENTION

Dry eye syndrome affects approximately three million people in the United States per year. While the syndrome rarely leads to blindness, it can become very debilitating and difficult to treat, some of the symptoms being, for example, stinging, burning, or scratchy sensations in your eyes. Some people may also experience sensitivity to light, redness in the eyes, a foreign body sensation in the eye, difficulty with wearing contact lenses, difficulty with night driving, watery eyes, which is the body's natural reaction or response to the irritation of dry eye, blurred vision, or eye fatigue. Treatment has classically centered on symptomatic relief with artificial tears, topical medications, with marginal results. It is therefore imperative that an area of a huge, conventionally unmet need, for a new paradigm of treatment for this condition, be developed.

A need therefore exists in the art for a new and improved medical device. An additional need exists in the art for a new and improved medical device which is specifically structured to treat dry eye syndrome. Another need exists in the art for a new and improved medical device which is specifically structured to treat dry eye syndrome and which does not comprise exogenous treatments. Yet another need exists in the art for a new and improved medical device which is specifically structured to treat dry eye syndrome by fluidically connecting the anterior chamber of the eye to the external ocular surface of the eye. Still another need exists in the art for a new and improved medical device which is specifically structured to treat dry eye syndrome by fluidically connecting the anterior chamber of the eye to the external ocular surface of the eye so as to permit aqueous humor, disposed within the anterior chamber of the eye, to flow outwardly therefrom and effectively bathe substantially the entire external ocular surface of the eye with aqueous humor. Still yet another need exists in the art for a new and improved medical device which is specifically structured to treat dry eye syndrome by fluidically connecting the anterior chamber of the eye to the external ocular surface of the eye so as to permit aqueous humor, disposed within the anterior chamber of the eye, to flow outwardly therefrom and effectively bathe substantially the entire external ocular surface of the eye with aqueous humor, thereby effectively providing the external ocular surface of the eye with sufficient lubrication.

A further need exists in the art for a new and improved medical device which is specifically structured to treat dry eye syndrome by fluidically connecting the anterior chamber of the eye to the external ocular surface of the eye so as to permit aqueous humor, disposed within the anterior chamber of the eye, to continuously flow outwardly therefrom and effectively bathe substantially the entire external ocular surface of the eye with aqueous humor, thereby effectively providing substantially the entire external ocular surface of the eye with the desired lubrication. A still further need exists in the art for a new and improved medical device which is specifically structured to treat dry eye syndrome by fluidically connecting the anterior chamber of the eye to the external ocular surface of the eye so as to permit aqueous humor, disposed within the anterior chamber of the eye, to flow outwardly therefrom and effectively bathe the entire external ocular surface of the eye with aqueous humor, thereby effectively providing substantially the entire external ocular surface of the eye with the desired lubrication so as to enable a continuous and physiologic treatment of dry eye syndrome.

OVERALL OBJECTIVES OF THE PRESENT INVENTION

An overall objective of the present invention is to provide a new and improved medical device. An additional overall objective of the present invention is to provide a new and improved medical device which is specifically structured to treat dry eye syndrome. Another overall objective of the present invention is to provide a new and improved medical device which is specifically structured to treat dry eye syndrome and which does not comprise exogenous treatments. Yet another overall objective of the present invention is to provide a new and improved medical device which is specifically structured to treat dry eye syndrome by fluidically connecting the anterior chamber of the eye to the external ocular surface of the eye. Still another overall objective of the present invention is to provide a new and improved medical device which is specifically structured to treat dry eye syndrome by fluidically connecting the anterior chamber of the eye to the external ocular surface of the eye so as to permit aqueous humor, disposed within the anterior chamber of the eye, to flow outwardly therefrom and effectively bathe substantially the entire external ocular surface of the eye with aqueous humor. Still yet another overall objective of the present invention is to provide a new and improved medical device which is specifically structured to treat dry eye syndrome by fluidically connecting the anterior chamber of the eye to the external ocular surface of the eye so as to permit aqueous humor, disposed within the anterior chamber of the eye, to flow outwardly therefrom and effectively bathe substantially the entire external ocular surface of the eye with aqueous humor, thereby effectively providing the external ocular surface of the eye with sufficient lubrication. A further overall objective of the present invention is to provide a new and improved medical device which is specifically structured to treat dry eye syndrome by fluidically connecting the anterior chamber of the eye to the external ocular surface of the eye so as to permit aqueous humor, disposed within the anterior chamber of the eye, to continuously flow outwardly therefrom and effectively bathe substantially the entire external ocular surface of the eye with aqueous humor, thereby effectively providing substantially the entire external ocular surface of the eye with the desired lubrication. A still further overall objective of the present invention is to provide a new and improved medical device which is specifically structured to treat dry eye syndrome by fluidically connecting the anterior chamber of the eye to the external ocular surface of the eye so as to permit aqueous humor, disposed within the anterior chamber of the eye, to flow outwardly therefrom and effectively bathe the entire external ocular surface of the eye with aqueous humor, thereby effectively providing substantially the entire external ocular surface of the eye with the desired lubrication so as to enable a continuous and physiologic treatment of dry eye syndrome.

SUMMARY OF THE INVENTION

In accordance with the principles and teachings of the present invention, and in accordance with a first embodiment of the present invention, an aqueous micro shunt is adapted to be inserted into the subconjunctival space of the human eye, and transit through the sclera of the human eye such that a distal end portion of the shunt is adapted to be disposed within the anterior chamber of the eye while a proximal end portion of the shunt is disposed externally of the eye, upon the sclera of the eye, so as to permit aqueous humor to flow from the anterior chamber of the eye, outwardly through the micro shunt, and then flow into the subconjunctival region of the eye so as to effectively treat dry eye syndrome, the aqueous humor transiting through the conjunctiva to physiologically cover the ocular surface. This trans-scleral disposition of the micro shunt allows the device to stabilize the scleral opening, and allows a secure consistent pathway from the anterior chamber to the subconjunctival space. The transit of fluid from the anterior chamber to the subconjunctival region is well known to be the basis for classic trabeculectomy surgery. This consistent outflow of aqueous fluid, which continues to percolate from a region of relatively higher pressure to a region of lower pressure, is the basis for pressure reduction upon which trabeculectomies or glaucoma surgeries are based. Such procedures have historically been the gold standard in glaucoma surgery. The device of the present invention, the aqueous micro shunt, is uniquely structured so as to safely transit anterior chamber aqueous fluid to the subconjunctival space while limiting the potential complication of too much fluid or too little fluid. A physiologic amount of aqueous fluid passively flowing from the anterior chamber to the superior subconjunctival space is the goal of the aqueous micro shunt. Controlling this outflow or the redistribution of the aqueous fluid is the premise of standard filtration surgery. We are utilizing this same aqueous fluid to further distribute it as it gently percolates from the subconjunctival space, transconjunctivally, and onto the ocular surface, to be distributed by the blinking of the eyelids, so as to effectively treat patients with moderate to severe dry eye syndrome. The conjunctiva acts as a semi-permeable one-way membrane to allow the gentle egress of aqueous fluid while still providing a protective membrane to prevent bacterial ingress and subsequent infection. Where exogenous treatments depend upon the application of tear supplements, the device of the present invention allows the constant replenishment of aqueous fluid onto the ocular surface of the patient's eye. In essence, this is the first surgical treatment for aqueous tear deficiency or dry eye syndrome wherein a consistent outflow of aqueous fluid is permitted to be dispersed in a substantially radially outwardly direction so as to effectively bathe all external corneal surface areas of the eye with the aqueous fluid.

In accordance with the specific principles and teachings of the present invention, the device comprises an aqueous micro shunt which includes a substantially flat plate which has a substantially semi-ovoid or semi-elliptical configuration, as can best be appreciated from a plan view thereof, and which is adapted to lie along the scleral surface under the conjunctiva, and a shaft which is adapted to be inserted through the scleral wall and into the anterior chamber of the eye. The plate is integrally mounted upon a proximal end of the shaft, and is disposed at a predetermined angular orientation with respect to the longitudinal axis of the shaft, such as, for example, at an angle of approximately 45°. The distal end of the shaft is appropriately pointed, so as to facilitate the ease of insertion through the sclera and into the anterior chamber of the eye, and is provided with a first hollow lumen which has a first substantially constant diameter and which extends from an opening at the distal end of the shaft to an axial position adjacent to the plate. The shaft also has a second hollow lumen which has a second substantially constant diameter which is substantially less than the first diameter of the first lumen and which has a first end fluidically connected to the first hollow lumen, while a second opposite end of the second hollow lumen is fluidically connected to a substantially radially extending slot defined within a substantially central portion of the flat plate, which is integrally mounted upon the proximal end of the shaft at the aforenoted predetermined angular orientation, such that the substantially radially extending slot is effectively interposed between upper and lower surface portions or sections of the flat plate. In view of the fact that the substantially radially extending slot effectively extends over a radial expanse of approximately superior 180°, this second proximal lumen, that fluidically connects the anterior chamber of the eye to the substantially radially extending slot defined within the substantially central portion of the plate, permits aqueous fluid to be dispersed over a substantially angular expanse of approximately the superior 180° so as to allow the substantial even distribution of the aqueous fluid across substantially the entire corneal region of the eye, as well as to prevent direct contact of the conjunctiva with the outflow lumen itself, thereby preventing obstruction.

It is to be noted that the first and second lumens have specific diametrical extents which facilitates a predetermined amount of outflow of the aqueous fluid from the anterior chamber of the eye, however, the ultimate volume of aqueous fluid that is dispersed is effectively limited by the diametrical extent of the second proximal lumen. The diametrical size of the second proximal lumen is important as it allows for a constant physiological outflow of the aqueous fluid, however, there are limits to the flow of the aqueous fluid so as not to allow hypotony with its litany of complications. The first or distal lumen is greater in its diametrical extent than the diametrical extent of the second proximal lumen so as to effectively utilize the pressure gradient which is greater inside the eye than that characteristic of the subconjunctival space, thereby facilitating constant outflow of the aqueous fluid. An alternate opening may be provided along or near the distal end of the shaft so as to allow aqueous fluid a secondary pathway into the lumen to be utilized should the primary opening in the distal end become obstructed. This consistency of transport and outflow of the aqueous fluid is the premise of the present invention so as to provide a source of renewable aqueous fluid for the surface of the eye.

It is also noted that the distal end of the shaft is angled so as to protect the iris from obstructing the opening and to keep the distal end of the shaft from engaging the endothelium of the cornea. The external surface of the shaft also comprises a series of beveled rings which allow for easy insertion while additionally helping to stabilize the shunt after placement within the eye. It is further noted that the external shaft is connected to the plate at a predetermined angle which is important so as to allow the plate to effectively lie flat along the scleral surface, and that the shaft entering the anterior chamber be equidistant from the iris and the corneal endothelium. Both of these structural features are important to avoid contact with the iris in that contact with the iris can cause chronic inflammation and pigment liberation, and in addition, contact with the corneal endothelium may cause loss of endothelial cells and corneal decompensation. Lastly, it is noted that in accordance with a second embodiment of the present invention, one or more through-holes or through-bores may be defined within the upper section of the plate and are fluidically connected to the slot defined within the central portion of the plate so as to also provide additional controlled outflows of the aqueous fluid along the external surface portion of the upper section of the plate and into the subconjunctival space. In summary, the aqueous micro shunt is a device which allows constant controlled flow of aqueous fluid from the anterior chamber of the eye to the subconjunctival space. By transit of the fluid through the conjunctiva, it will be redistributed onto the surface so as to assist in the treatment of patients with moderate to severe dry eye syndrome.

BRIEF DESCRIPTIONS OF THE DRAWINGS

Various other objects, features and attendant advantages of the present invention will be more fully appreciated from the following detailed description when considered in connection with the accompanying drawings in which like reference characters designate like or corresponding parts throughout the several views, and wherein.

DETAILED DESCRIPTION OF THE ILLUSTRATED EMBODIMENT

Figure 1:
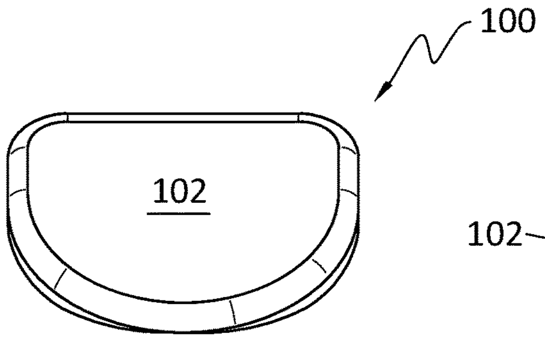
FIG. 1 is a top plan view of a first embodiment of a new and improved aqueous micro shunt as developed and constructed in accordance with the principles and teachings of the present invention.
Figure 2:
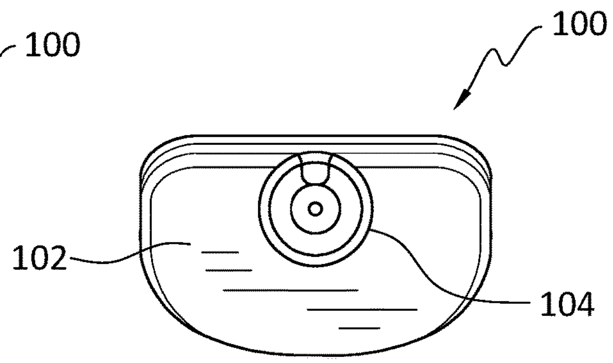
FIG. 2 is a bottom plan view of the new and improved aqueous micro shunt as illustrated within FIG. 1.
Figure 3:
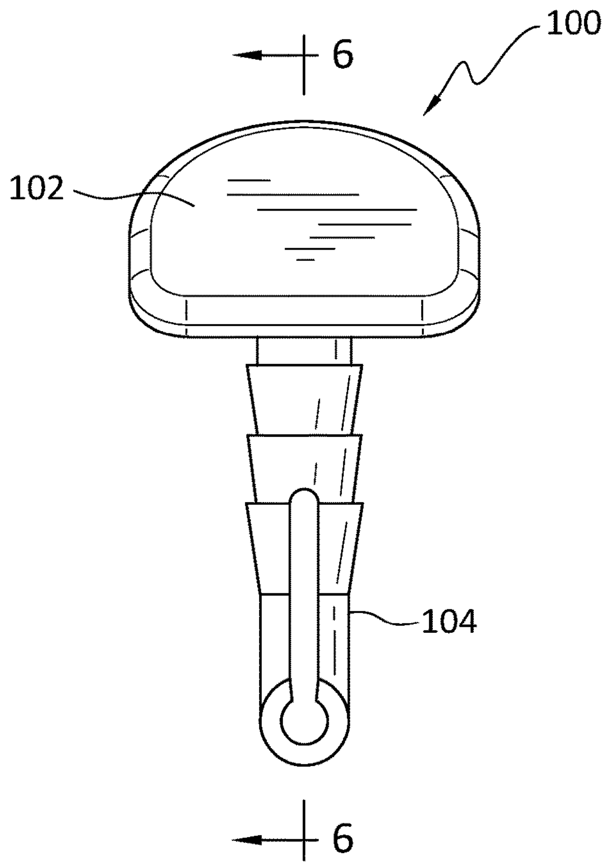
FIG. 3 is a front elevational view of the new and improved aqueous micro shunt as illustrated within FIG. 1.
Figure 4:
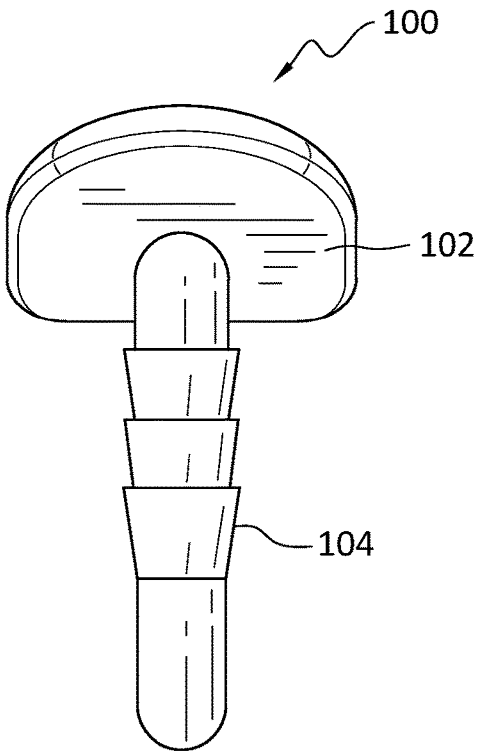
FIG. 4 is a rear elevational view of the new and improved aqueous micro shunt as illustrated within FIG. 1.
Figure 5:
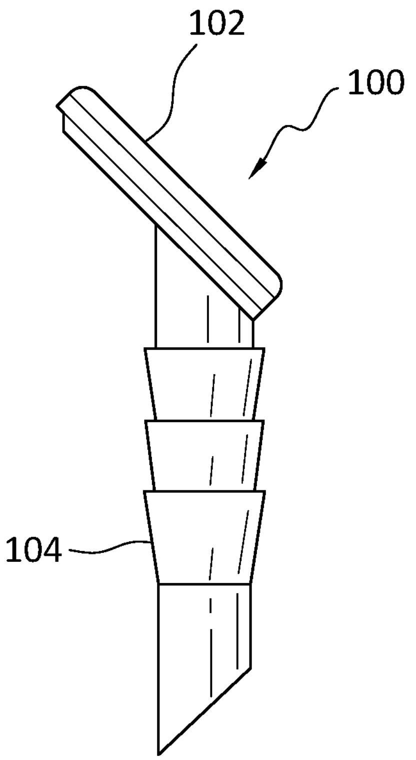
FIG. 5 is a side elevational view of the new and improved aqueous micro shunt as illustrated within FIG. 1.
Figure 6:
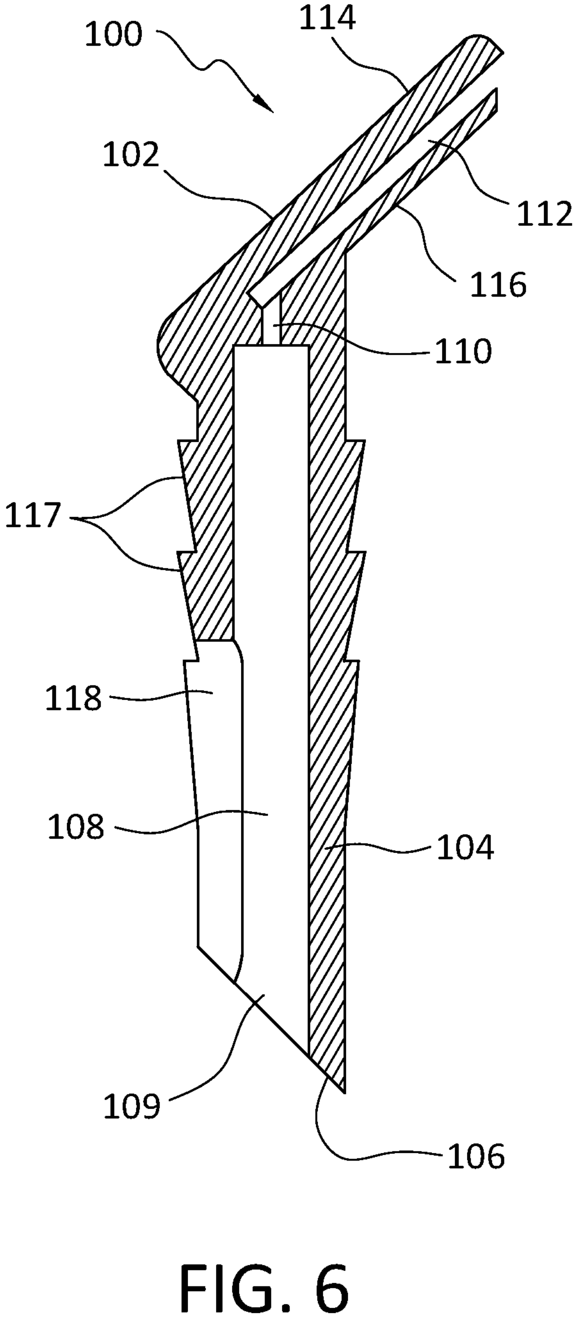
FIG. 6 is a cross-sectional view of the new and improved aqueous micro shunt as illustrated within FIG. 1 and as taken along the line 6-6 of FIG. 3.
Figure 7:
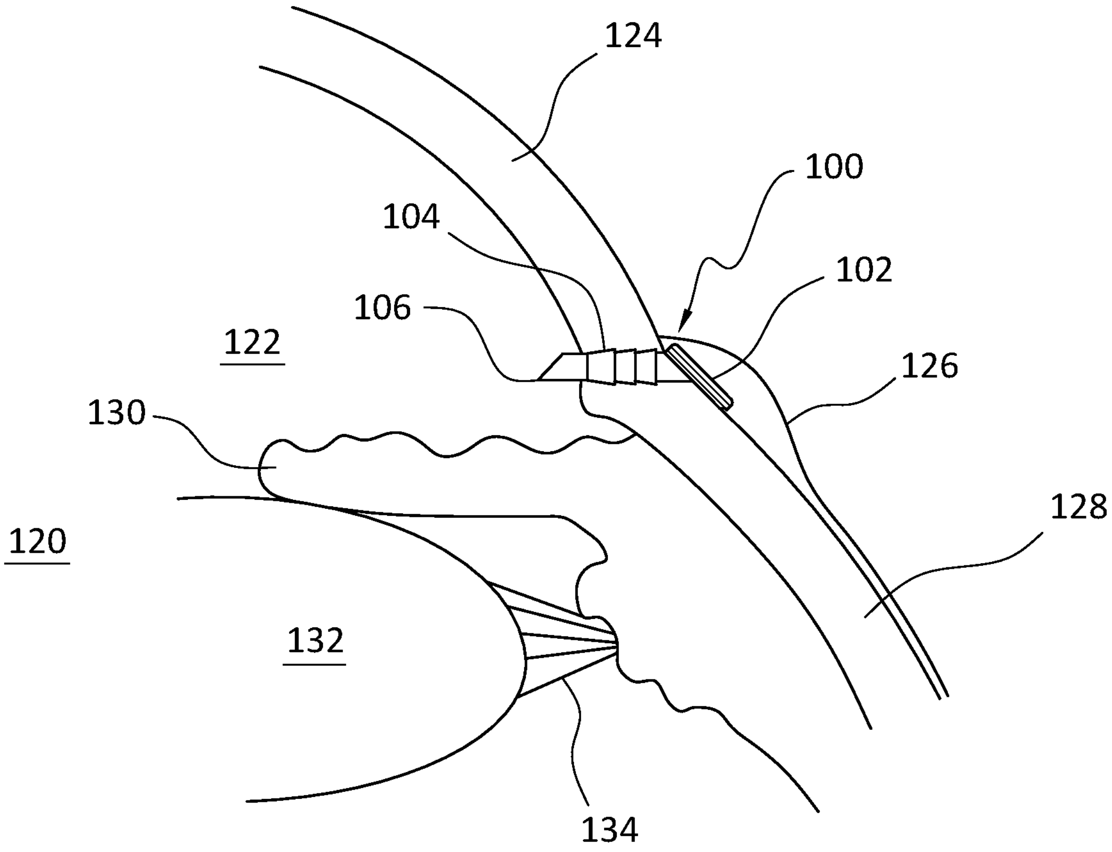
FIG. 7 is a schematic view illustrating how the new and improved aqueous micro shunt of the present invention is disposed when inserted into a person's eye so as to provide the flow of aqueous fluid to the subconjunctival space of the eye.

With reference first being made to FIG. 1, the new and improved aqueous micro shunt is disclosed and is generally indicated by the reference character 100. More particularly, it is seen that the new and improved aqueous micro shunt 100 is seen to comprise a substantially flat plate 102, which has a substantially semi-ovoid or semi-elliptical configuration, as can best be appreciated from the plan and front elevational views of FIGS. 1 and 3, and which is adapted to lie along the scleral surface under the conjunctiva, as can best be appreciated from FIG. 7, and a shaft 104 which is integrally attached to the substantially flat plate 102 and which is adapted to be inserted through the scleral wall of the eye and into the anterior chamber of the eye, as can also be best appreciated from FIG. 7. The plate 102 is integrally mounted upon a proximal end of the shaft 104, and is disposed at a predetermined angular orientation with respect to the longitudinal axis of the shaft 104, such as, for example, at a 45° angle, so as to permit the plate to be properly disposed along the scleral surface once the aqueous micro shunt 100 is inserted into the person's eye as disclosed within FIG. 7. The distal end of the shaft is sharply pointed, as at 106, so as to facilitate ease of insertion into the anterior chamber of the eye, and is provided with a first, axially extending hollow lumen 108 which has a first substantially constant diameter and which extends from an opening 109 at the distal end 106 of the shaft 104 to an axial position adjacent to the plate 102. The shaft 104 also has a second hollow lumen 110 defined therein which has a second substantially constant diameter which is substantially less than the first diameter of the first lumen 108 and which has a first end fluidically connected to the first hollow lumen 108, while a second opposite end of the second hollow lumen 110 is fluidically connected to a substantially radially extending slot 112 which is defined within a substantially central portion of the flat plate 102 which is integrally mounted upon the proximal end of the shaft 104 so as to be disposed at the aforenoted predetermined angular orientation. The substantially radially extending slot 112 defined within the plate 102 is effectively interposed between upper and lower surface sections 114,116 of the flat plate 102. This is a critically unique structural connection because it is to be realized that in lieu of the aqueous fluid from the anterior chamber of the eye exiting the second lumen 110 and the plate 102 in a direction effectively coaxial with the axial extents of the first and second lumens 108, 110 defined within the shaft 104, to the contrary, the aqueous fluid effectively engages or impacts the undersurface portion of the upper plate section 114 and is effectively deflected or redirected radially outwardly through means of the substantially radially extending slot 112. It is to be additionally noted that the substantially radially extending slot 112 effectively extends over a radial expanse of approximately the superior 180°, and therefore, the second proximal lumen 110, that fluidically connects the anterior chamber of the eye to the substantially radially extending slot 112 defined within the substantially central portion of the plate 102, permits aqueous fluid to be dispersed over a substantially angular expanse of approximately the superior 180° so as to allow the substantial even distribution of the aqueous fluid into the subconjunctival region of the eye, whereby the fluid will then migrate transconjunctivally and onto the ocular surface so as to present an autologous aqueous layer upon the corneal surface to be redistributed by the physiologic blinking of the eyelids.

It is to be noted that the first and second lumens 108, 110 have specific diametrical extents which effectively create a pressure gradient that facilitates a predetermined amount of outflow of the aqueous fluid from the anterior chamber of the eye, however, the ultimate volume of aqueous fluid that is dispersed is effectively limited by the diametrical extent of the second proximal lumen 110. The diametrical size of the second proximal lumen 110 is critical as it allows for a constant physiological outflow of the aqueous fluid, however, there are practical and medical limits of the outflow of the aqueous fluid so as not to cause hypotony with its litany of complications. The first or distal lumen 108 is greater in its diametrical extent than the diametrical extent of the second proximal lumen 110 so as to effectively utilize such pressure gradient which is greater inside the eye than that characteristic of the subconjunctival space, thereby facilitating the constant outflow of the aqueous fluid from the anterior chamber of the eye and onto the outer ocular surface of the eye. This consistent transport and outflow of the aqueous fluid is the premise of the present invention so as to provide a source of renewable aqueous fluid for the outer ocular surface of the eye. The external surface of the shaft also comprises a series of beveled rings 117 which allow for a secure insertion while additionally helping to stabilize the aqueous micro shunt 100 after placement within the eye. It is lastly noted that the shaft 104 is also provided with a secondary opening 118 so as to permit aqueous fluid to enter the first primary lumen 108 should, for example, the opening 109 to the first primary lumen 108, as defined at the pointed distal end portion 106 of the shaft 104, become obstructed for some reason. For completeness of this disclosure, in furtherance of the understanding of the present invention, and to further disclose how the aqueous micro shunt 100 is actually disposed within a person's eye so as to provide the necessary flow of the aqueous humor from the anterior chamber of the eye onto the outer ocular surface of the eye, reference is quickly made to FIG. 7 wherein a cross-section of a human eye is schematically illustrated.

More particularly, it is seen that a human eye 120 comprises an anterior chamber 122 within which aqueous humor is disposed. The cornea of the eye is disclosed at 124, while the conjunctiva and sclera are respectively noted at 126 and 128. The iris is disclosed at 130, while the lens is disclosed at 132. Lastly, the zonule fibers are disclosed at 134. The aqueous micro shunt 100 is also disclosed, as has been described. Accordingly, and in summary, the aqueous micro shunt 100 is adapted to be inserted into the subconjunctival space 126 of the human eye 120, and transit through the sclera 128 of the human eye 120, such that a distal end portion 106 of the shunt 100 is adapted to be disposed within the anterior chamber 122 of the eye 120, while a proximal end portion of the shunt 100 is disposed externally of the eye 120, upon the sclera 128 of the eye, so as to permit aqueous humor to flow from the anterior chamber 122 of the eye 120, outwardly through the micro shunt 100, and then flow into the subconjunctival region 126 of the eye 120 so as to effectively treat dry eye syndrome, the aqueous humor eventually being redistributed over the ocular surface.

This trans-scleral disposition of the micro shunt 100 allows the device to secure the scleral opening, and allows a consistent pathway from the anterior chamber 122 of the eye 120 to the subconjunctival region 126 of the eye 120. The transit of fluid from the anterior chamber 122 of the eye 120 to the subconjunctival region 126 of the eye 120 is well known to be the basis for classic trabeculectomy surgery. This consistent outflow of aqueous fluid, which continues to percolate from a region of relatively higher pressure to a region of lower pressure, is the basis for pressure reduction upon which trabeculectomies or glaucoma surgeries are based. Such procedures have historically been the gold standard in glaucoma surgery. The aqueous micro shut 100 of the present invention is uniquely structured so as to safely transmit anterior chamber aqueous fluid to the subconjunctival space 126 while limiting the downside of too much fluid or too little fluid. A physiologic amount of aqueous fluid passively flowing from the anterior chamber 122 of the eye 120 to the superior subconjunctival space 126 is the goal of the aqueous micro shunt 100. Controlling this outflow or the redistribution of the aqueous fluid is the premise of standard filtration surgery. We are utilizing this same aqueous fluid to further distribute it as it gently percolates from the subconjunctival space 126, transconjunctivally, and onto the ocular surface 128, to be distributed by the blinking of the eyelids, so as to effectively treat patients with moderate to severe dry eye syndrome. Where exogenous treatments depend upon the application of tear supplements, the aqueous micro shunt 100 of the present invention allows the constant replacement of aqueous fluid onto the ocular surface 128 of the patient's eye.

In essence, this is the first surgical treatment for aqueous tear deficiency or dry eye syndrome wherein a consistent outflow of aqueous fluid is permitted to be dispersed in a substantially radially outwardly direction so as to effectively bathe all external corneal surface areas 124 of the eye 120 with the aqueous fluid. It is also noted that as a result of the unique structure of the aqueous micro shunt 100, comprising the shaft 104 and the integral mounting of the angled plate 102 thereon, direct contact of the conjunctiva with the outflow lumen 110 itself, is prevented, thereby preventing any obstruction of the outflow lumen 110. It is lastly to be noted that, as can best be appreciated from FIG. 7, since the aqueous micro shunt 100 is inserted into the eye at the limbus, or at a position immediately adjacent to the limbus, but on the scleral side of the limbus as opposed to on the corneal side of the limbus, then the plate 102 of the aqueous micro shunt 100 must be angled relative to the shaft 104 such that when the distal pointed end 106 of the shaft 104 is inserted into the eye, the shaft 104 will effectively be disposed parallel to the iris 130 so as to protect the iris from being injured by the distal pointed end 106 of the shaft 104, so as to prevent the distal end 106 of the shaft 104 from engaging the endothelium of the cornea 124, and for preventing the opening 108 at the pointed distal end 106 of the shaft 104 from being obstructed by the iris 130.

Figure 8:
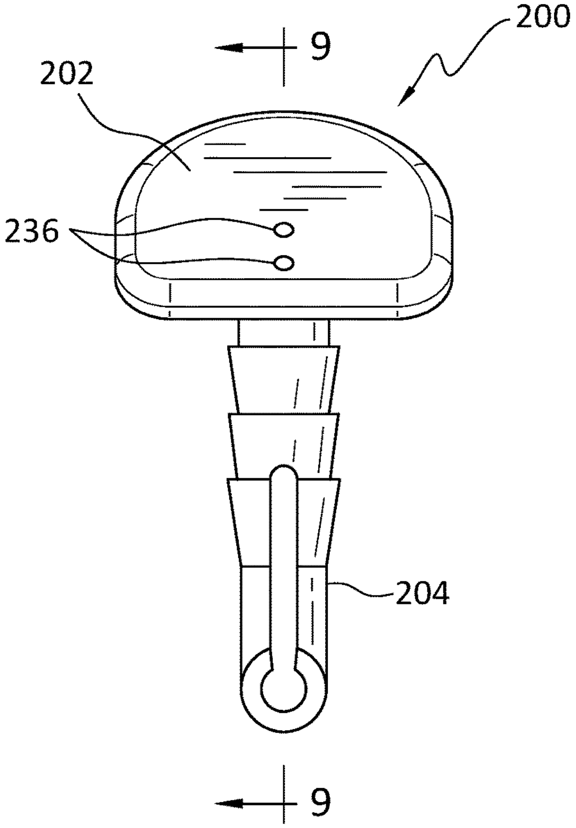
FIG. 8 is a front elevational view, similar to that of FIG. 3, of a second embodiment of the new and improved aqueous micro shunt.
Figure 9:
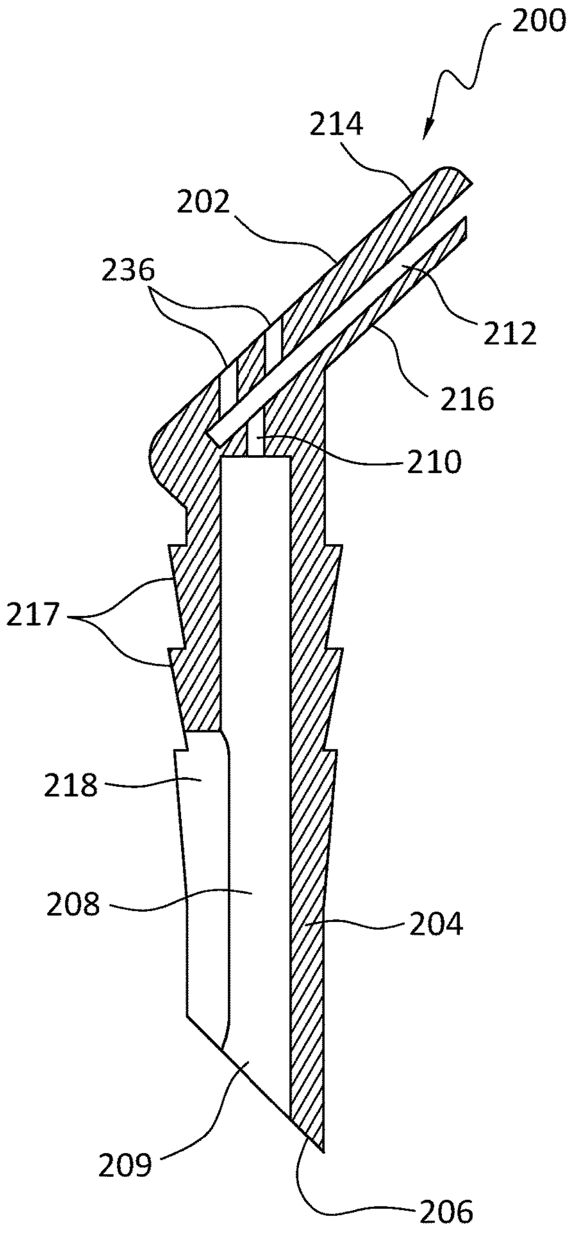
FIG. 9 is a cross-sectional view, similar to that of FIG. 6, but taken along the lines 9-9 of FIG. 8.

With reference lastly being made to FIGS. 8 and 9, a second embodiment of the present invention is disclosed and is generally indicated by the reference character 200. The second embodiment 200 of the present invention is essentially the same as the first embodiment 100, except for a significant difference which will be discussed more fully immediately hereinafter, and accordingly, component parts of the second embodiment 200 of the present invention which correspond to component parts of the first embodiment 100 of the present will be designated by corresponding reference numbers, however, they will be within the 200 series. More particularly, the significant difference between the second embodiment 200 of the present invention and the first embodiment 100 of the present resides in the fact that in accordance with the principles and teachings of the second embodiment 200 of the present invention, one or more through-holes or through-bores 236 are defined or provided within the upper plate section 214 of the plate 202 so as to be in fluidic communication with the slot 212 defined within the central portion of the plate 202. In this manner, in addition to the aqueous fluid flowing outwardly from the slot 212 defined within the central portion of the plate 202, aqueous fluid may likewise percolate out from the through-holes or through-bores 236 defined within the upper plate section 214 of the plate 202 flow downwardly over the external surface portion of the plate 202, and into the subconjunctival space of the eye 120.

Obviously, many variations and modifications of the present invention are possible in light of the above teachings. It is therefore to be understood that within the scope of the appended claims, the present invention may be practiced otherwise than as specifically described herein.

What is claimed as new and desired to be protected by Letters Patent, is:

1. An aqueous micro shunt for treating dry eye syndrome, comprising:

an axially oriented shaft, defined around a longitudinal axis, for insertion through a scleral wall portion of an eye and into an anterior chamber of the eye and having an open distal end adapted to be fluidically connected to aqueous humor contained within the anterior chamber of the eye;

at least one lumen defined within said axially oriented shaft and having a first end fluidically connected to said open distal end of said shaft;

a plate fixedly mounted at a predetermined angle upon a proximal end of said axially oriented shaft so as to be disposed in a sub-conjunctival space of an eye, and wherein said plate has a substantially semi-elliptical configuration; and a single slot, defined within said plate, which is fluidically connected to a second end of said at least one lumen, wherein said single slot is disposed at said predetermined angle, as defined by said plate fixedly mounted upon said proximal end of said axially oriented shaft, and wherein said single slot has a continuous radial expanse of approximately 180° so as to be capable of dispersing aqueous fluid throughout a substantially 180° expanse whereby aqueous fluid can flow from the anterior chamber of the eye, through said at least one lumen defined within said axially elongated shaft, and outwardly through said single slot defined within said plate so as to flow over an ocular surface portion of the eye and thereby treat dry eye syndrome.

2. The shunt as set forth in claim 1, wherein said at least one lumen comprises:

a first axially oriented lumen defined within said axially oriented shaft and having a first end fluidically connected to said open distal end of said shaft;

a second axially oriented lumen defined within said axially oriented shaft and having a first end fluidically connected to a second end of said first axially oriented lumen, and a second end fluidically connected to said slot defined within said plate.

3. The shunt as set forth in claim 2, wherein:

said first lumen has a diametrical extent which is greater than a diametrical extent of said second lumen such that a pressure gradient is effectively created that facilitates a predetermined amount of outflow of the aqueous fluid from the anterior chamber of the eye, through said first and second lumens, and out through said slot defined within said plate.

4. The shunt as set forth in claim 1, wherein:

said predetermined angle of said plate, mounted upon said proximal end of said axially oriented shaft, is disposed at an angle of approximately 45° with respect to said longitudinal axis of said axially oriented shaft.

5. The shunt as set forth in claim 4, wherein:

said plate, mounted upon said proximal end of said axially oriented shaft, is disposed at said angle of approximately 45° with respect to said longitudinal axis of said axially oriented shaft such that when said shunt is inserted into the eye, said pointed distal end of said axially oriented shaft will not engage or injure an iris portion of the eye.

6. The shunt as set forth in claim 1, wherein:

said slot, defined within said plate, is defined between upper and lower portions of said plate and extends parallel to said upper and lower portions of said plate.

7. The shunt as set forth in claim 6, wherein:

said slot, defined between said upper and lower portions of said plate and extending parallel to said upper and lower portions of said plate, effectively prevents the aqueous fluid from the anterior chamber of the eye from flowing axially outwardly, as the aqueous fluid flows through said at least one lumen defined within said axially oriented shaft, but effectively deflects the flow of the aqueous fluid such that the flow of the aqueous fluid flows outwardly from said aqueous micro shunt in a substantially radial direction.

8. The shunt as set forth in claim 1, wherein:

said axially oriented shaft, defined around said longitudinal axis, has a pointed distal end for facilitating insertion of said axially oriented shaft through the scleral wall portion of the eye and into the anterior chamber of the eye.

9. The shunt as set forth in claim 1, wherein:

at least one through-bore is defined within an upper section of said plate so as to be in fluidic communication with said slot, whereby aqueous fluid can flow from the anterior chamber of the eye, through said at least one lumen defined within said axially elongated shaft, and outwardly through said slot defined within said plate, as well as through said at least one through-bore defined within said upper section of said plate, so as to flow over an ocular surface portion of the eye and thereby treat dry eye syndrome.

10. The shunt as set forth in claim 9, wherein:

said at least one through-bore defined within said upper section of said plate comprises a multiplicity of through-bores defined within said upper section of said plate.

* * * * *